United States Patent
Sheth et al.

(10) Patent No.: US 8,486,983 B2
(45) Date of Patent: *Jul. 16, 2013

(54) SELF-EMULSIFYING FORMULATIONS OF CETP INHIBITORS

(75) Inventors: Agam R. Sheth, Lansdale, PA (US); Bhagwant Rege, Collegeville, PA (US); Soumojeet Ghosh, Lansdale, PA (US); Laman L. Alani, Lansdale, PA (US); Maria T. Cruanes, Lansdale, PA (US); Craig A. McKelvey, Ambler, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/085,745

(22) PCT Filed: Dec. 5, 2006

(86) PCT No.: PCT/US2006/046503
§ 371 (c)(1),
(2), (4) Date: May 29, 2008

(87) PCT Pub. No.: WO2007/067593
PCT Pub. Date: Jun. 14, 2007

(65) Prior Publication Data
US 2009/0186926 A1    Jul. 23, 2009

Related U.S. Application Data

(60) Provisional application No. 60/742,451, filed on Dec. 5, 2005.

(51) Int. Cl.
*A61K 31/421* (2006.01)
(52) U.S. Cl.
USPC .......................................... 514/376

(58) Field of Classification Search
USPC .......................................... 514/376
See application file for complete search history.

(56) References Cited

U.S. PATENT DOCUMENTS

| 6,096,338 A | 8/2000 | Lacy et al. |
| 6,962,931 B2 * | 11/2005 | Gumkowski et al. ......... 514/313 |
| 2003/0072801 A1 | 4/2003 | Curatolo |
| 2006/0040999 A1 * | 2/2006 | Ali et al. ....................... 514/376 |
| 2010/0041724 A1 | 2/2010 | Miller et al. |

FOREIGN PATENT DOCUMENTS

| WO | WO 92 21348 | 12/1992 |
| WO | WO 03 000295 | 1/2003 |
| WO | WO 2005 011634 | 2/2005 |
| WO | WO 2006 014357 | 2/2006 |

* cited by examiner

*Primary Examiner* — San-Ming Hui
*Assistant Examiner* — Kathrien Cruz
(74) *Attorney, Agent, or Firm* — James L. McGinnis; Catherine D. Fitch

(57) ABSTRACT

A liquid formulation for oral administration of the CETP inhibitor of formula (I) has improved bioavailability compared with conventional solid formulations. The formulation comprises the CETP inhibitor, or a pharmaceutically acceptable salt thereof; an oil; and one or more nonionic surfactants having a hydrophilic lipophilic balance (HLB)>10.

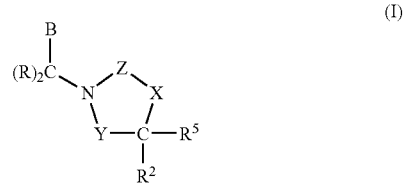

(I)

7 Claims, No Drawings

SELF-EMULSIFYING FORMULATIONS OF CETP INHIBITORS

CROSS REFERENCE TO RELATED APPLICATIONS

This application is a U.S. National Phase application under 35 U.S.C. §371 of PCT Application No. PCT/US2006/046503, filed Dec. 5, 2006, which claims priority under 35 U.S.C. §119(e) from U.S. Application No. 60/742,451, filed Dec. 5, 2005.

FIELD OF THE INVENTION

This invention relates to formulations of a class of compounds which are CETP inhibitors and to concentrated solutions containing the active compound which readily disperse in vivo when they are administered to a patient, so that the CETP inhibitor is readily absorbed by the patient.

BACKGROUND OF THE INVENTION

Atherosclerosis and its clinical consequences, coronary heart disease (CHD), stroke and peripheral vascular disease, represent a truly enormous burden to the health care systems of the industrialized world. In the United States alone, approximately 13 million patients have been diagnosed with CHD, and greater than one half million deaths are attributed to CHD each year. Further, this toll is expected to grow over the next quarter century as the average age of the population increases and as an epidemic in obesity and diabetes continues to grow.

Inhibition of cholesteryl ester transfer protein (CETP) is a promising new approach to reducing the incidence of atherosclerosis. Statins have been important in reducing the incidence of CHD by reducing LDL-cholesterol (the "bad cholesterol"), but are relatively ineffective at raising HDL-cholesterol ("the good cholesterol"). CETP inhibitors raise HDL-cholesterol and may also lower-LDL-cholesterol, and may therefore provide a potent new tool for reducing CHD and atherosclerosis in the general population. Combination therapy using CETP inhibitors and statins may also become a valuable tool for controlling both HDL and LDL levels, which may make it possible to both treat and prevent atherosclerosis, and perhaps even to reverse the formation of atherosclerotic plaques. Currently, Pfizer's torcetrapib is the only CETP inhibitor that is known to be in advanced Phase III clinical trials.

CETP inhibitors in general are very lipophilic. The compounds are generally nearly insoluble in water and in aqueous bodily fluids. Bioavailability of CETP inhibitors using conventional tablet formulations generally is poor. Oral formulations therefore need to be developed that will make the compounds bioavailable when they are administered to a patient. Liquid formulations of a particularly potent class of CETP inhibitors are described herein. The formulations disperse in water, resulting in higher absorption of the drug by the patient. These formulations are self-emulsifying formulations, yielding emulsions or microemulsions. The formulations are commonly referred to as self-emulsifying or self-microemulsifying drug delivery systems (SEDD's or SMEDD's).

SUMMARY OF THE INVENTION

The present invention provides orally bioavailable self-emulsifying and self-microemulsifying formulations of the following class of CETP inhibitors, including pharmaceutically acceptable salts, represented by Formula I:

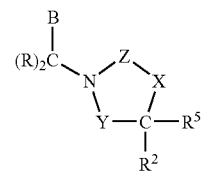

I

In the compounds of Formula I,

Y is selected from —C(=O)— and —(CRR$^1$)—;

X is selected from —O—, —NH—, —N(C$_1$-C$_5$alkyl)-, and —(CRR$^6$)—;

Z is selected from —C(=O)—, —S(=O)—, and —C(=N—R$^9$)—, wherein R$^9$ is selected from the group consisting of H, —CN, and —C$_1$-C$_5$alkyl optionally substituted with 1-11 halogens;

Each R is independently selected from the group consisting of H, —C$_1$-C$_5$ alkyl, and halogen, wherein —C$_1$-C$_5$ alkyl is optionally substituted with 1-11 halogens;

B is selected from the group consisting of A$^1$ and A$^2$, wherein A$^1$ has the structure:

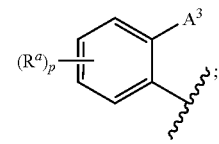

R$^1$ and R$^6$ are each independently selected from H, —C$_1$-C$_5$ alkyl, halogen, and —(C(R)$_2$)$_n$A$^2$, wherein —C$_1$-C$_5$ alkyl is optionally substituted with 1-11 halogens;

R$^2$ is selected from the group consisting of H, —C$_1$-C$_5$ alkyl, halogen, A$^1$, and —(C(R)$_2$)$_n$A$^2$, wherein —C$_1$-C$_5$ alkyl is optionally substituted with 1-11 halogens;

Wherein one of B and R$^2$ is A$^1$; and one of B, R$^1$, R$^2$, and R$^6$ is A$^2$ or —(C(R)$_2$)$_n$A$^2$; so that the compound of Formula I comprises one group A$^1$ and one group A$^2$;

A$^3$ is selected from the group consisting of:
(a) an aromatic ring selected from phenyl and naphthyl;
(b) a phenyl ring fused to a 5-7 membered non-aromatic cycloalkyl ring, which optionally comprises 1-2 double bonds;
(c) a 5-6-membered heterocyclic ring having 1-4 heteroatoms independently selected from N, S, O, and —N(O)—, and optionally also comprising 1-3 double bonds and a carbonyl group, wherein the point of attachment of A$^3$ to the phenyl ring to which A$^3$ is attached is a carbon atom; and
(d) a benzoheterocyclic ring comprising a phenyl ring fused to a 5-6-membered heterocyclic ring having 1-2 heteroatoms independently selected from O, N, and S, and optionally also having 1-2 double bonds (in addition to the double bond of the fused phenyl ring) wherein the point of attachment of A$^3$ to the phenyl ring to which A$^3$ is attached is a carbon atom;

A$^2$ is selected from the group consisting of:
(a) an aromatic ring selected from phenyl and naphthyl;
(b) a phenyl ring fused to a 5-7 membered non-aromatic cycloalkyl ring, which optionally comprises 1-2 double bonds;

(c) a 5-6-membered heterocyclic ring having 1-4 heteroatoms independently selected from N, S, O, and —N(O)—, and optionally also comprising 1-3 double bonds and a carbonyl group;

(d) a benzoheterocyclic ring comprising a phenyl ring fused to a 5-6-membered heterocyclic ring having 1-2 heteroatoms independently selected from O, N, and S, and optionally also having 1-2 double bonds (in addition to the double bond of the fused phenyl ring); and (e) a —$C_3$-$C_8$ cycloalkyl ring optionally having 1-3 double bonds;

wherein $A^3$ and $A^2$ are each optionally substituted with 1-5 substituent groups independently selected from $R^a$;

Each $R^a$ is independently selected from the group consisting of —$C_1$-$C_6$ alkyl, —$C_2$-$C_6$ alkenyl, —$C_2$-$C_6$ alkynyl, —$C_3$-$C_8$ cycloalkyl optionally having 1-3 double bonds, —$OC_1$-$C_6$alkyl, —$OC_2$-$C_6$ alkenyl, —$OC_2$-$C_6$ alkynyl, —$OC_3$-$C_8$ cycloalkyl optionally having 1-3 double bonds, —C(=O)$C_1$-$C_6$alkyl, —C(=O)$C_3$-$C_8$ cycloalkyl, —C(=O)H, —$CO_2$H, —$CO_2C_1$-$C_6$alkyl, —C(=O)S$C_1$-$C_6$alkyl, —OH, —$NR^3R^4$, —C(=O)$NR^3R^4$, —$NR^3$C(=O)$OC_1$-$C_6$alkyl, —$NR^3$C(=O)$NR^3R^4$, —S(O)$_x$$C_1$-$C_6$ alkyl, —S(O)$_y$$NR^3R^4$, —$NR^3$S(O)$_{y6}$/ $NR^3R^4$, halogen, —CN, —$NO_2$, and a 5-6-membered heterocyclic ring having 1-4 heteroatoms independently selected from N, S, and O, said heterocyclic ring optionally also comprising a carbonyl group and optionally also comprising 1-3 double bonds, wherein the point of attachment of said heterocyclic ring to the ring to which $R^a$ is attached is a carbon atom, wherein said heterocyclic ring is optionally substituted with 1-5 substituent groups independently selected from halogen, —$C_1$-$C_3$ alkyl, and —$OC_1$-$C_3$ alkyl, wherein —$C_1$-$C_3$ alkyl and —$OC_1$-$C_3$ alkyl are optionally substituted with 1-7 halogens;

wherein for compounds in which $R^a$ is selected from the group consisting of —$C_1$-$C_6$ alkyl, —$C_2$-$C_6$ alkenyl, —$C_2$-$C_6$ alkynyl, —$C_3$-$C_8$ cycloalkyl optionally having 1-3 double bonds, —$OC_1$-$C_6$alkyl, —$OC_2$-$C_6$ alkenyl, —$OC_2$-$C_6$ alkynyl, —$OC_3$-$C_8$ cycloalkyl optionally having 1-3 double bonds, —C(=O)$C_1$-$C_6$alkyl, —C(=O)$C_3$-$C_8$ cycloalkyl, —$CO_2C_1$-$C_6$alkyl, —C(=O)S$C_1$-$C_6$alkyl, —$NR^3$C(=O)$OC_1$-$C_6$ alkyl, and —S(O)$_x$$C_1$-$C_6$ alkyl, $R^a$ is optionally substituted with 1-15 halogens and is optionally also substituted with 1-3 substituent groups independently selected from (a) —OH, (b) —CN, (c) —$NR^3R^4$, (d) —$C_3$-$C_8$ cycloalkyl optionally having 1-3 double bonds and optionally substituted with 1-15 halogens, (e) —$OC_1$-$C_4$alkyl optionally substituted with 1-9 halogens and optionally also substituted with 1-2 substituent groups independently selected from —$OC_1$-$C_2$ alkyl and phenyl, (f) —$OC_3$-$C_8$ cycloalkyl optionally having 1-3 double bonds and optionally substituted with 1-15 halogens, (g) —$CO_2$H, (h) —C(=O)$CH_3$, (i) —$CO_2C_1$-$C_4$alkyl which is optionally substituted with 1-9 halogens, and (j) phenyl which is optionally substituted with 1-3 groups independently selected from halogen, —$CH_3$, —$CF_3$, —$OCH_3$, and —$OCF_3$;

with the proviso that when B is $A^1$, and X and Y are —$CH_2$—, and Z is —C(=O)—, and $R^2$ is phenyl which has a substituent $R^a$ in the 4-position, wherein $R^a$ is —$OC_1$-$C_6$alkyl which is optionally substituted as described above, then there are no other $R^a$ substitutents on $R^2$ in which $R^a$ is selected from —OH, —$OC_1$-$C_6$alkyl, —$OC_2$-$C_6$ alkenyl, —$OC_2$-$C_6$ alkynyl, and —$OC_3$-$C_8$ cycloalkyl optionally having 1-3 double bonds, all of which are optionally substituted as described above;

n is 0 or 1;
p is an integer from 0-4;
x is 0, 1, or 2;
y is 1 or 2;

$R^3$ and $R^4$ are each independently selected from H, —$C_1$-$C_5$ alkyl, —C(=O)$C_1$-$C_5$ alkyl and —S(O)$_y$$C_1$-$C_5$ alkyl, wherein —$C_1$-$C_5$ alkyl in all instances is optionally substituted with 1-11 halogens; and $R^5$ is selected from the group consisting of H, —OH, —$C_1$-$C_5$ alkyl, and halogen, wherein —$C_1$-$C_5$ alkyl is optionally substituted with 1-11 halogens.

In the compounds of Formula I and in subsequent groups of compounds, alkyl, alkenyl, and alkynyl groups can be either linear or branched, unless otherwise stated.

DETAILED DESCRIPTION OF THE INVENTION

In preferred subsets, X is selected from the group consisting of —O—, —NH—, and —N($C_1$-$C_3$alkyl)-. X may also be selected from the group consisting of —O—, —NH—, and —N($CH_3$). In highly preferred subsets, X is O.

In many embodiments, Z is —C(=O)—.

A preferred subgroup of compounds has Formula Ie, including pharmaceutically acceptable salts thereof

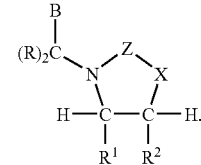

Ie

In compounds of formula Ie, X is selected from the group consisting of —O—, —NH—, —N($C_1$-$C_5$alkyl)- and —($CH_2$)—;

Z is selected from the group consisting of —C(=O)—, —S(O)$_2$—, and —C(=N—$R^9$)—, wherein $R^9$ is selected from the group consisting of H, —CN, and $C_1$-$C_5$alkyl optionally substituted with 1-11 halogens;

Each R is independently selected from the group consisting of H and —$CH_3$;

B is selected from the group consisting of $A^1$ and $A^2$, wherein $A^1$ has the structure:

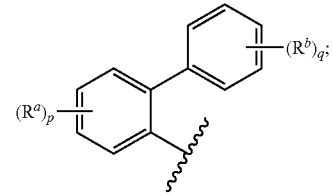

$R^1$ is selected from the group consisting of H, —$C_1$-$C_5$ alkyl, and —(C(R)$_2$)$_n$$A^2$, wherein —$C_1$-$C_5$ alkyl is optionally substituted with 1-11 halogens;

$R^2$ is selected from the group consisting of H, —$C_1$-$C_5$ alkyl, $A^1$, and —(C(R)$_2$)$_n$$A^2$, wherein —$C_1$-$C_5$alkyl is optionally substituted with 1-11 halogens;

Wherein one of B and $R^2$ is $A^1$; and one of B, $R^1$, and $R^2$ is $A^2$ or —(C(R)$_2$)$_n$$A^2$; so that the compound of Formula Ie comprises one group $A^1$ and one group $A^2$;

$A^2$ is selected from the group consisting of phenyl, cyclohexyl, and pyridyl, wherein $A^2$ is optionally substituted with 1-2 substituent groups independently selected from halogen, —C$_1$-C$_4$ alkyl, and —CN, wherein —C$_1$-C$_4$ alkyl is optionally substituted with 1-3 halogens;

Each R$^a$ is independently selected from the group consisting of —C$_1$-C$_3$ alkyl and halogen, wherein —C$_1$-C$_3$ alkyl is optionally substituted with 1-3 halogens;

Each R$^b$ is independently selected from the group consisting of Cl, F, —C$_1$-C$_4$ alkyl, and —OC$_1$-C$_4$alkyl, wherein —C$_1$-C$_4$alkyl and —OC$_1$-C$_4$alkyl are optionally substituted with 1-5 F;

n is 0 or 1;
p is an integer from 0-2; and
q is an integer from 0-3.

Subsets of compounds having formula Ie include compounds of formula If, Ig, and Ih, and pharmaceutically acceptable salts thereof:

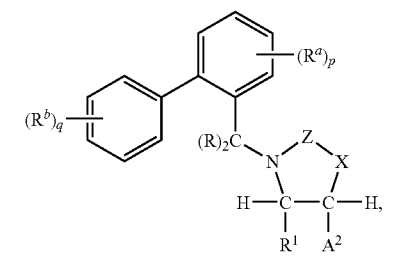

If

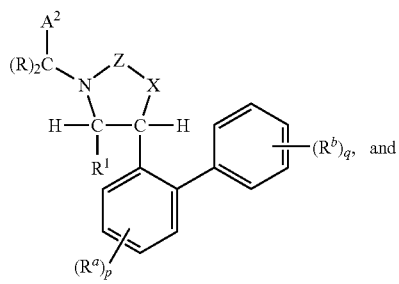

Ig

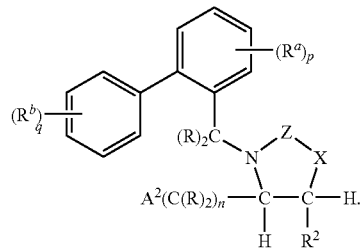

Ih

In the compounds of formula If, Ig, and Ih, R$^1$ and R$^2$ are each independently selected from H and —C$_1$-C$_5$ alkyl, wherein —C$_1$-C$_5$ alkyl is optionally substituted with 1-11 halogens. Other groups are as defined previously.

In subsets of the compounds described above, A$^2$ may be selected from the group consisting of phenyl, cyclohexyl, and pyridyl, wherein A$^2$ is optionally substituted with 1-2 substituent groups independently selected from halogen, —CH$_3$—CF$_3$, and —CN.

In subsets of the compounds described above, each R$^a$ independently is selected from the group consisting of —CF$_3$ and Cl.

In subsets of the compounds described above, each R$^b$ is independently selected from the group consisting of C$_1$-C$_3$ alkyl, —OCH$_3$, and F.

In subsets of the compounds described above, R$^1$ and R$^2$ are each independently selected from the group consisting of H and —C$_1$-C$_2$ alkyl.

In subsets of the compounds described above, X is selected from —O—, —NH—, —N(CH$_3$)—, and —CH$_2$—.

In subsets of the compounds described above, Z is selected from the group consisting of —C(=O)—, —S(O)$_2$—, and —C(=N—CN)—.

In subsets of the compounds described above, p is 1.

In subsets of the compounds described above, q is 2 or 3.

A subset of compounds defined previously comprises compounds having formula Ii, and pharmaceutically acceptable salts thereof:

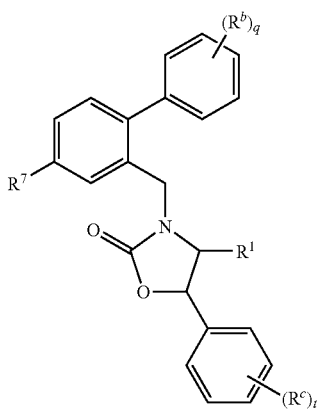

Ii

In formula Ii, R$^7$ is selected from the group consisting of Cl and —CF$_3$;

R$^c$ is selected from the group consisting of halogen, —CH$_3$—CF$_3$, and —CN; and t is an integer from 0-2. Other groups are as defined previously.

A subset of compounds defined previously comprises compounds having formula Ij, or a pharmaceutically acceptable salt thereof:

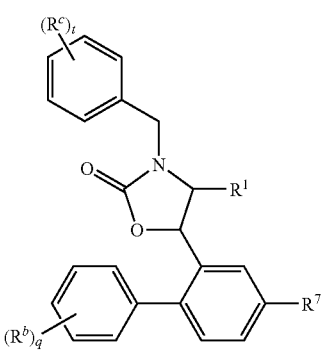

Ij

In formula Ii, R$^7$ is selected from the group consisting of Cl and —CF$_3$;

R$^c$ is selected from the group consisting of halogen, —CH$_3$—CF$_3$, and —CN; and t is an integer from 0-2. Other groups are as defined previously.

A particularly preferred embodiment of this invention is directed to the compound having formula II, including pharmaceutically acceptable salts thereof:

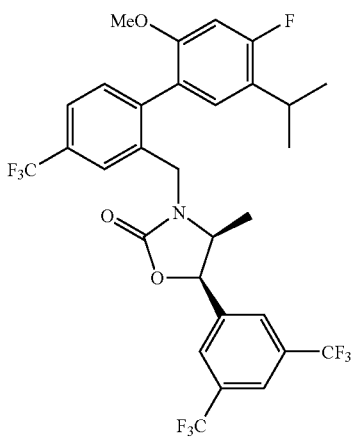

The compounds described above having formula I-Ij and formula II are disclosed in commonly assigned PCT Applications published as WO2006/014357 and WO2006/014413 and in U.S. application Ser. No. 11/173,295, published as US2006/0040999. These compounds and the formulations of the compounds disclosed herein are potent CETP inhibitors. When they are administered to a patient, the amount of HDL-cholesterol increases and the amount of LDL-cholesterol decreases. The compounds and the formulations of the compounds are useful in treating diseases which are characterized by low-HDL and/or high-LDL, or can be treated or ameliorated by raising HDL and/or reducing LDL such as hypercholesterolemia, hyperlipidemia, and atherosclerosis. Furthermore, administration of the compounds and formulations described herein does not cause an increase in blood pressure. Doses in humans that will be therapeutically effective in raising HDL and lowering LDL are in the range of 20 mg to 200 mg, such as for example 20 mg, 25 mg, 30 mg, 40 mg, 50 mg, 60 mg, 70 mg, 80 mg, 90 mg, 100 mg, 110 mg, 120 mg, 130 mg, 140 mg, 150 mg, 160 mg, 180 mg and 200 mg, administered once, twice or three times a day.

The formulations of this invention, which are preconcentrates for oral administration that generally will yield an emulsion or microemulsion upon mixing with water, such as in aqueous bodily fluids, comprise:

(1) The active compound, or a pharmaceutically acceptable salt thereof, as described above, having formulae I-Ij or II;

(2) a fatty acid ester oil component, which comprises medium chain ($C_6$-$C_{12}$) and/or long chain ($C_{14}$-$C_{20}$) fatty acid monoesters and/or diesters of glycerol (i.e. monoglycerides and/or diglycerides) and of propylene glycol; monoesters, diesters, and triesters of sorbitan, and mixtures thereof; and optionally also comprises triglycerides of medium chain and/or long chain fatty acids; and (3) one or more nonionic surfactants having a hydrophilic lipophilic balance (HLB)>10, and preferably >12.

The compositions optionally may have a hydrophilic co-solvent in addition to the fatty acid ester oil phase (2) and the phase having one or more nonionic surfactants (3) with HLB>10. The optional hydrophilic co-solvent may be included in this formulation to help dissolve the API. A hydrophilic co-solvent is usually very water soluble or miscible with water. Examples of common hydrophilic co-solvents include triacetin, propylene carbonate, transcutol, ethyl lactate, triethyl citrate, N-methyl-2-pyrrolidinone, dimethylisosorbide, glycofurol, ethanol, and ethoxyethylene glycol. The amount of hydrophilic co-solvent, if present, is generally in an amount up to 10% of the total weight of the fatty acid ester oil phase and the nonionic surfactant(s). In other embodiments, the amount of hydrophilic co-solvent is present in an amount up to 5% of the total weight of the fatty acid ester oil phase. In many preferred embodiments, there is no hydrophilic co-solvent.

The amount of active compound (API) of formula I-Ij or II can vary over a wide range, limited at the lower end by the necessity of having enough API to be able to administer a therapeutically effective amount, and at the upper end by solubility in the liquid carrier phase. Typically the amount of API will be in the range of 1-30%, generally 5% to 25%, and most often 10% to 20% by weight.

The fatty acid ester oil phase (2) and the nonionic surfactants (3) having HLB>10, not including the API and preservative, are generally present in a ratio of 90:10 to 10:90; often in a ratio of 4:1 to 1:4; and often in a ratio of 3:1 to 1:3.

The optional triglyceride in some embodiments is not present. In many embodiments, the triglyceride is present in the fatty acid ester oil phase at a level of about 25%-75% of the total fatty acid ester oil phase, and in some embodiments, at a level of about 40%-60% of the total fatty acid ester oil phase. In some embodiments, the triglyceride is present at a level of about 45%-55% of the total fatty acid ester oil phase.

The fatty acid monoesters and diesters of glycerol and of propylene glycol, and the fatty acid monoesters, diesters, and triesters of sorbitan are surfactants having a low hydrophilic-lipophilic balance (HLB) value of less than 10, and most often between 3 and 10. The optional fatty acid ester triglycerides are not surfactants.

The high HLB non-ionic surfactants have an HLB value >10, and generally between 12 and 20. In many embodiments, the high HLB surfactants comprise polyoxyethylene units as part of their structure. The high HLB surfactants typically have 15-50 oxyethylene units, and often have 20-35 oxyethylene units.

The CETP inhibitors used in these formulations are poorly soluble in water. They are however generally soluble in the fatty acid ester oils used in making the preconcentrates and in solutions of the fatty acid ester oils and the nonionic surfactants. The liquid formulations of the CETP inhibitors are in general homogeneous solutions.

Examples of fatty acid monoglycerides and diglycerides include Imwitor 742 (glyceryl mono-/di-caprylate/caprate), Imwitor 988 (glyceryl mono-/dicaprylate), Imwitor 308 (glyceryl monocaprylate), Imwitor 191 (glyceryl monostearate), Capmul MCM (glyceryl monocaprylate/caprate), Capmul GMO (glyceryl monooleate), Capmul GDL (glyceryl dilaurate), Maisine (glyceryl monooleate), and Peceol (glyceryl monooleate). Caprate and caprylate mono and diglycerides are preferred, including Imwitor 742, Imwitor 988, Imwitor 308, and Capmul MCM. Imwitor 742 is especially preferred. Corresponding mono- and diglycerides are available from other manufacturers under other trademarks and tradenames. The mono and diglycerides in general have hydrophilic and lipophilic regions in their molecular structures and act as surfactants having low HLB, where low HLB is defined as less than or equal to 10. Similarly the propylene glycol monoesters and diesters and the sorbitan monoesters, diesters, and triesters have hydrophilic and lipophilic regions in their molecular structure and act as surfactants having low HLB, defined as less than or equal to 10.

Examples of propylene glycol mono- and diesters include Captex 200, Miglyol 840, and Neobee M-20 (all comprise propylene glycol dicaprylate/caprate), Lauroglycol (propylene glycol monolaurate), Mirpyl (propylene glycol monolaurate) and Capmul PG8 (propylene glycol monocaprylate with up to about 5% propylene glycol dicaprylate). The caprate and/or caprylate esters and diesters are preferred, such as Capmul PG8, Captex 200, Miglyol 840, and Neobee M-20. Corresponding propylene glycol mono- and diesters are also available from other manufacturers under other trademarks and tradenames.

Examples of sorbitan monoesters, diesters, and triesters include sorbitan monooleate (e.g. Span-80), sorbitan monopalmitate (e.g. Span-40), sorbitan monolaurate (e.g. Span-20), sorbitan monostearate (e.g. Span-60), sorbitan trioleate (e.g. Span-85), sorbitan sesquioleate (e.g. Arlacel-C), sorbitan tristearate (e.g. Span-65), sorbitan monoisostearate (e.g. Crill 6), and sorbitan sesquistearate (e.g. Nikkol SS-15). In some embodiments, sorbitan monoleate (HLB 4.3) is the preferred sorbitan ester.

Examples of triglycerides include medium chain triglycerides (C6-C12), such as fractionated coconut oils, including Miglyol 812 (56% caprylic (C8) and 36% capric (C10) triglycerides), Miglyol 810 (68% C8 and 28% C10 triglycerides), Neobee M5, Captex 300, Captex 355, and Crodamol GTCC. Examples of long chain triglycerides (C14-C20) include vegetable oils, such as safflower, corn, soybean, olive, cotton seed, sunflower seed, arachis, palm and rapeseed oils. Preferred triglycerides are C8-C10 triglycerides, such as Miglyol 812. Corresponding triglycerides are also available from other manufacturers under other trademarks and tradenames. A preferred vegetable oil is corn oil.

Examples of surfactants (3) having HLB greater than 10 include polyethylene glycol (PEG) sorbitan fatty acid esters, such as PEG-20 sorbitan monolaurate (polysorbate 20, Tween-20, HLB 17), PEG-20 sorbitan monopalmitate (Tween-40, HLB 16), PEG-20 sorbitan monostearate (Tween-60, HLB 15) and PEG-20 sorbitan monooleate (polysorbate 80, Tween-80, HLB 15). Other examples of high HLB surtantants include castor oils containing PEG chains, such as PEG-35 castor oil (Cremophor EL, HLB 12-14), PEG40 hydrogenated castor oil (Cremophor RH40, HLB 13) and PEG-60 hydrogenated castor oil (Cremophor 60, HLB 15). Another preferred high HLB non-ionic surfactant is Vitamin E tocopheryl polyethylene glycol succinate (Vitamin E TPGS). Preferred high HLB surfactants include Tween-80, Cremophor EL, Cremophor RH40, Vitamine E TPGS, and equivalent surfactants having other trademarks and tradenames. In some embodiments mixtures of Tween-80 and Cremophor EL are used.

In some embodiments of the invention, the fatty acid ester oil phase (2) comprises a mixture of (i) caprylate and caprate esters of propylene glycol, such as Capmul PG-8, which has an HLB of 3-3.5.

In some embodiments of the invention, the high HLB surfactant phase (3) comprises a mixture of (i) PEG sorbitan fatty acid esters, such as Tween-80, and (ii) castor oil and/or hydrogenated castor oils containing PEG chains, such as Cremophor EL and Cremophor RH40.

In some embodiments, the fatty acid ester oil phase (2) is a mixture of (a) mixed mono- and diglycerides of capric and caprylic acids (e.g. Imwitor 742), which has an HLB of 8-10; and (b) mixed triglycerides of capric and caprylic acids (e.g. Miglyol 812).

In many embodiments, the amounts of the components of the formulations are; (1) 1-20% by weight of API; (2) 10-70% by weight of the fatty acid ester oil component; and (3) 35-75% by weight of the high HLB non-ionic surfactants.

The compositions described above generally do not require a hydrophilic co-solvent, such as is often required in these kinds of compositions, where the hydrophilic co-solvent has a relatively low molecular weight, such as ethanol, triacetin, and ethoxyethylene glycol. A hydrophilic co-solvent is optional, but in preferred embodiments is not present.

The formulations readily form emulsions or microemulsions when they are mixed with water or aqueous solutions that simulate the conditions within the digestive system. When microemulsions are formed, they are stable and appear homogeneous to the eye. There is no observed cloudiness. The particle size of the oil droplets of the microemulsion made from the preconcentrate of Example 1 is 16-18 nm as measured by laser light scattering.

These formulations provide improved bioavailability compared with other formulations, as shown by the fact that the active ingredient is absorbed more completely in these formulations after oral administration. Surprisingly, the formulations that yield emulsions such as Example 3, provide bioavailability that is comparable to that of the microemulsions.

Furthermore, conventional formulations comprising the CETP inhibitors used herein show a significant "food effect," which results in large differences in the amount and rate of absorption into the body depending on when the patient was last fed, how soon the patient eats after oral administration of the drug, and whether the patient takes the drug with a meal. The formulations disclosed herein exhibit a reduced food effect.

EXAMPLES

The following examples are provided to more fully illustrate the invention and are not to be construed as limiting the scope of the invention, which is defined by the appended claims.

Examples of formulations are described below. The formulations exhibit improved bioavailability when administered orally to a patient. Bioavailability is determined in vivo by dosing trial formulations of the active pharmaceutical agent (API) to monkeys (normally three monkeys per trial) at a dose of 1 mg/kg of the API and then measuring the amount of API in the serum or blood as a function of time. Comparisons are made with other formulations of the API, such as solid formulations with conventional excipients, or with other liquid formulations as described herein. These formulations are generally emulsion and microemulsion preconcentrates, and regardless of whether the formulations form emulsions or microemulsions in aqueous systems, those that were tested all exhibit improved bioavailability of the drug (compound II) compared with conventional formulation.

Example 1

The formulation comprises (wt %) (1) 8.75% Compound II, (2) 26.25% Capmul PG8, (3) 32.5% Cremophor EL, and (4) 32.5% Tween 80. The antioxidant BHA (butylated hydroxyanisole) (about 0.01%) is added to the final formulation. The final composition not including Compound II or the antioxidant comprises (1) 28.8% Capmul PG8, (2) 35.6% Cremophor EL, and (3) 35.6% Tween 80.

The formulation is made on a scale of about 1 gram by first dissolving Compound II in Capmul PG8 at room temperature and then combining the solution of Compound II and Capmul PG8 with a solution of Tween 80 and Cremophor EL, which is made separately by stirring the two liquid surfactants together at room temperature Example 2

The formulation comprises (wt %) (1) 10% Compound II, (2) 22.5% Imwitor 742, (3) 22.5% Miglyol 812, (4) 36%

Cremophor EL, and (5) 9% Tween 80. The antioxidant BHA (butylated hydroxyanisole) (about 0.01%) is added to the final formulation. The final composition not including Compound II or the antioxidant comprises (1) 25% Imwitor 742, (2) 25% Miglyol 812, (3) 40% Cremophor EL, and (4) 10% Tween 80.

The formulation is made on a scale of about 1 gram by making two solutions having the proportions described above. One solution comprises Compound II and the two glycerides and is made as follows. Imwitor 742 (a waxy solid) is heated to about 40° C. to yield a liquid melt. Miglyol 812, which is a liquid, is then added to the molten Imwitor 742 at about 35-40° C. to yield a clear solution. Compound II is then added, and the mixture is stirred overnight at about 35° C., yielding a clear solution of Compound II, Imwitor 742, and Miglyol 812. The solution does not solidify or phase separate at room temperature.

A second solution is made by combining Tween 80 and Cremophor EL at room temperature for about 30 minutes and stirring until the two surfactants are completely mixed.

The two solutions from above are then combined and stirred at room T, yielding a clear solution.

Example 3

The formulation comprises (wt %) (1) 20% Compound II, (2) 40% Imwitor 742, and (3) 40% polysorbate 80 (Tween 80). The antioxidant BHA (butylated hydroxyanisole) (about 0.01%) is also included in the final formulation. The final composition not including Compound II or the antioxidant comprises (1) 50% Imwitor 742, and (2) 50% Tween 80.

The composition is made by the following procedure:

Imwitor 742 is melted in a 40° C. oven overnight. The Tween 80 is weighed into a stainless steel container equipped with a variable speed mixer. With continuous mixing, the molten Imwitor 742 and solid butylated hydroxyanisole are stirred into the Tween 80, and stirring is continued until the mixture is homogeneous, and for a minimum of 15 minutes. The temperature is maintained in the range of room temperature to 50° C., but is not kept at 50° C. for more than 8 hrs. With continuous mixing, compound II is added, and mixing is continued until the mixture is homogeneous, for a minimum of 15 minutes. If necessary, the container is covered and the mixing is continued overnight. Mixing is judged as complete when the mixture is visually clear. The formulation is deaerated and then transferred into hard gelatin capsules or soft gelatin capsules. It is filtered before being transferred if suspended solids are observed.

Example 4

The formulation comprises (wt %) (1) 20% Compound II, (2) 28% corn oil, (3) 24% sorbitan monooleate, and (4) 28% Cremophor EL. The antioxidant BHA (butylated hydroxyanisole) (about 0.01%) is also included in the final formulation. The final composition, not including Compound II or the antioxidant, comprises (1) 35% corn oil, (2) 30% sorbitan monooleate, and (3) 35% Cremophor EL.

The composition is made by the following procedure:

Corn oil is weighed and transferred into a jacketed stainless steel/glass container equipped with a variable speed mixer. Sorbitan monooleate, Cremophor EL, and butylated hydroxyanisole are added to the corn oil with continuous mixing. Mixing is continued for at least 15 minutes, and until the solid BHA has dissolved and the mixture is homogeneous. The temperature of the jacketed vessel is increased to 55° C. With continuous mixing, compound II is added, and the mixture is stirred at 55° C. until it is homogeneous. Temperature probes are used to monitor the temperature. The temperature is kept at 55° C. during drug solubilization, with the time at 55° C. not exceeding 8 hrs. If necessary, the container is covered, and mixing is continued overnight at room temperature. Mixing is judged as complete when the mixture is visually clear. The formulation is deaerated and then transferred into hard gelatin capsules or soft gelatin capsules. It is filtered before being transferred if suspended solids are observed.

Example 5

The formulation comprises (wt %) (1) 20% Compound II, (2) 10% Imwitor 742, (3) 10% Miglyol 812, and (4) 60% Vitamin E TPGS. The antioxidant BHA (butylated hydroxyanisole) (about 0.01%) is also included in the final formulation. The final composition, not including Compound II or the antioxidant, comprises (1) 12.5% Imwitor 742, (2) 12.5% Miglyol 812, and (3) 75% Vitamin E TPGS.

The formulation is made as follows:

Imwitor 742 is melted by stirring overnight in an oven at 40° C. Vitamin E TPGS is weighed into a jacketed stainless steel/glass container equipped with a variable speed mixer. The vitamin E TPGS is melted by heating it in the jacketed vessel at 55° C. With continuous mixing, the desired amounts of molten Imwitor 742, Miglyol 812 and butylated hydroxyanisole are added to the molten Vitamin E TPGS, which is maintained at 55° C., and mixed until the mixture is homogeneous, for a minimum of 15 minutes. The formulation temperature is maintained at 55° C. Temperature probes are used to monitor the temperature. With continuous mixing, compound II is added, and the mixture is stirred at 55° C. until it is homogeneous. The temperature is kept at 55° C. during drug solubilization. The time at 55° C. should not exceed 8 hrs. If necessary for complete solubilization, the container is covered, and mixing is continued overnight at 35-40° C. Completion of mixing is judged visually. The formulation is deaerated and then transferred into hard gelatin capsules at 55° C. or soft gelatin capsules at 32-33° C. If necessary, the solution is filtered before being transferred.

In the examples above, drug loadings of the formulations are readily adjusted in the range of 10-20%, and more generally 5%-25%, by varying the amount of Compound II that is added to the mixture and varying the amounts of the other components proportionally.

The pharmokinetics of the formulations of Examples 1-5 were measured in Rhesus monkeys as described above. The formulation of Example 3 was used with a drug loading of 10% rather than 20%. The formulations were administered to monkeys at a dose of 1 mg/kg. The AUC, $C_{max}$ and $T_{max}$ for all 5 formulations were determined by measuring the drug concentration as a function of time for 24 hours. $AUC_{0-24}$ for all five formulations was in the range 1.9-2.7 μM*hr. The maximum concentration $C_{max}$ was 0.31 μM for Example 1 and 0.13-0.15 μM for the formulations of Examples 2-5, with $T_{max}$ occurring at 2.0 hrs for Example 1, at 4.0-6.0 hrs for the formulations of Examples 24, and at 18 hrs for Example 5.

What is claimed is:

1. An orally bioavailable self-emulsifying or self-microemulsifying pharmaceutical formulation comprising:
   (1) 1-30% by weight of a compound which is a CETP inhibitor, or a pharmaceutically acceptable salt thereof;
   (2) a fatty acid ester oil phase, wherein said fatty acid ester oil phase comprises one or more compounds selected from the group consisting of fatty acid monoglycerides, fatty acid diglycerides, fatty acid monoesters of propylene glycol, fatty acid diesters of propylene glycol, fatty acid monoesters of sorbitan, fatty acid diesters of sorbitan, fatty acid triesters of sorbitan, and mixtures thereof, wherein said fatty acids are selected from medium chain $C_6$-$C_{12}$ fatty acids and long chain $C_{14}$-$C_{20}$ fatty acids, and mixtures thereof, wherein said fatty acid ester oil phase optionally also comprises one or more triglycerides of medium chain $C_6$-$C_{12}$ fatty acids, long chain $C_{14}$-$C_{20}$ fatty acids, and mixtures thereof; and (3) one or more nonionic surfactants having a hydrophilic lipophilic balance (HLB) in the range of 10-20;

wherein the ratio of the fatty acid ester oil phase and the one or more nonionic surfactants is 1:4 to 4:1 by weight; wherein the formulation does not include a cosolvent selected from the group consisting of triacetin, propylene carbonate, transcutol, ethyl lactate, triethyl citrate, N-methyl-2-pyrrolidinone, dimethylisosorbide, glycofurol, ethanol, and ethoxyethylene glycol;

wherein the CETP inhibitor has formula II:

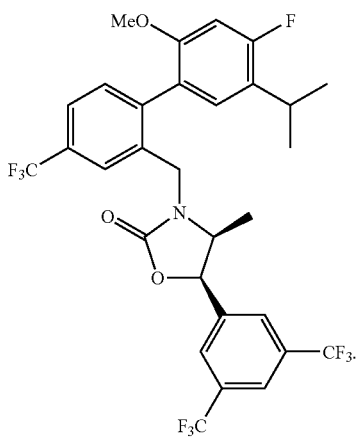

II

2. The formulation of claim 1, comprising 5% to 25% by weight of the compound of formula II.

3. The formulation of claim 1, comprising (1) 10% to 20% by weight of the compound of formula II, or a pharmaceutically acceptable salt thereof;

(2) a fatty acid ester oil phase; and (3) one or more nonionic surfactants, having an HLB in the range of 10-20; wherein the ratio of the fatty acid oil ester phase, and the one or more nonionic surfactants is 3:1 to 1:3 by weight.

4. The formulation of claim 2, wherein the nonionic surfactant is selected from PEG-40 hydrogenated castor oil (Cremophor RH40); PEG-35 castor oil (Cremophor EL); polysorbate 80 (Tween-80); Vitamin E TPGS; and mixtures thereof.

5. The formulation of claim 4, wherein the fatty acid ester oil phase comprises one or more medium chain monoglycerides, medium chain diglycerides, medium chain monoesters of propylene glycol, medium chain diesters of propylene glycol, or long chain sorbitan monoesters; and optionally one or more medium chain triglycerides or long chain triglycerides.

6. The formulation of claim 4, wherein the fatty acid ester oil phase comprises one or more caprylate and caprate mono- and diglycerides, or a mixture thereof; and one or more caprylate and caprate triglycerides, or a mixture thereof; and the nonionic surfactant is a mixture of polysorbate 80 and PEG-35 castor oil.

7. The formulation of claim 2, wherein the fatty acid ester oil phase comprises one or more caprylate and caprate mono- and diglycerides, or a mixture thereof; the non-ionic surfactant is polysorbate 80; and the formulation does not include a triglyceride.

* * * * *